(12) United States Patent
Tanabe

(10) Patent No.: US 8,721,551 B2
(45) Date of Patent: May 13, 2014

(54) WIRELESS ULTRASOUND DIAGNOSTIC SYSTEM

(75) Inventor: Tsuyoshi Tanabe, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/279,403

(22) Filed: Oct. 24, 2011

(65) Prior Publication Data

US 2012/0101389 A1    Apr. 26, 2012

(30) Foreign Application Priority Data

Oct. 26, 2010 (JP) ................. 2010-239420

(51) Int. Cl.
*A61B 8/14* (2006.01)

(52) U.S. Cl.
USPC .......................... 600/459; 600/437

(58) Field of Classification Search
USPC .................. 600/437–469
See application file for complete search history.

(56) References Cited

U.S. PATENT DOCUMENTS

| | | | |
|---|---|---|---|
| 2009/0036780 A1* | 2/2009 | Abraham | 600/459 |
| 2009/0179757 A1* | 7/2009 | Cohn et al. | 340/542 |
| 2010/0160785 A1 | 6/2010 | Poland et al. | |
| 2010/0191121 A1* | 7/2010 | Satoh et al. | 600/459 |
| 2011/0061466 A1* | 3/2011 | Nishino | 73/632 |

FOREIGN PATENT DOCUMENTS

| | | |
|---|---|---|
| JP | 08056946 A | 3/1996 |
| JP | 2003122458 A | 4/2003 |
| JP | 2007-275087 A | 10/2007 |
| JP | 2008023007 A | 2/2008 |
| JP | 2009-060992 A | 3/2009 |
| JP | 2010012035 A | 1/2010 |
| JP | 2010528698 A | 8/2010 |

OTHER PUBLICATIONS

Notification of Reasons for Refusal, dated Sep. 18, 2012, issued in corresponding JP Application No. 2010-239420, 6 pages in English and Japanese.

* cited by examiner

*Primary Examiner* — Sanjay Cattungal
(74) *Attorney, Agent, or Firm* — Sughrue Mion, PLLC

(57) ABSTRACT

An ultrasound diagnostic system includes at least one oscillator unit, at least one communication unit which processes and wirelessly transmits reception signals outputted from the at least one oscillator unit and from which the at least one oscillator unit is detachable, and a diagnostic apparatus body which acquires the reception signals through wireless communication with the at least one communication unit to generate an ultrasound image of the reception signals. The diagnostic apparatus body acquires identification information of the at least one oscillator unit and the at least one communication unit to establish the wireless communication with the at least one wireless communication unit so that the reception signals of a probe are wirelessly transmitted to the diagnostic apparatus body. The ultrasound diagnostic system has replaceable oscillator units and is capable of flexible and smooth wireless connection between the diagnostic apparatus body and a probe having desired settings.

17 Claims, 4 Drawing Sheets

WIRELESS ULTRASOUND DIAGNOSTIC SYSTEM

BACKGROUND OF THE INVENTION

The present invention relates to a wireless ultrasound diagnostic system capable of wireless transmission of signals received from an ultrasound probe to the body of a diagnostic apparatus. The invention more specifically relates to a wireless ultrasound diagnostic system capable of suitably dealing with the replacement of an oscillator unit in a wireless ultrasound probe and the simultaneous presence of a wireless ultrasound probe and a wired ultrasound probe.

Heretofore, ultrasound diagnostic apparatuses that use ultrasound images have been put to practical use in the medical field. In general, this type of ultrasound diagnostic apparatus comprises an ultrasound probe having a built-in oscillator array and an apparatus body connected to the ultrasound probe. The ultrasound probe transmits ultrasonic waves toward a subject, receives ultrasonic echoes from the subject, and the apparatus body electrically processes the reception signals to generate an ultrasound image.

An ultrasound diagnostic apparatus including an ultrasound probe and a diagnostic apparatus body connected by wireless communication has recently been developed in order to eliminate cumbersome handling of a communication cable of connecting the ultrasound probe with the diagnostic apparatus body for the improvement of operability.

As described in JP 2007-275087 A, an example of such a wireless ultrasound diagnostic apparatus comprises an ultrasound probe including a transmitter/receiver which transmits and receives ultrasonic waves to obtain reception signals for an ultrasound image and a wireless transmitter which wirelessly transmits probe identification information and the reception signals to a diagnostic apparatus body, and the apparatus body including an apparatus controller which controls in accordance with the probe identification information and an image forming section which forms the ultrasound image based on the reception signals.

On the other hand, an ultrasound diagnostic apparatus is used for making various diagnoses in subjects but the scan mode of the ultrasound probes or the proper ultrasound frequency range may often differ with the purpose of diagnosis or the site to be diagnosed.

It is therefore possible to prepare a plurality of types of ultrasound probes and connect an ultrasound probe selected according to the purpose of diagnosis to the apparatus body. However, it is more costly to prepare the plurality of types of ultrasound probes beforehand because the ultrasound probes are generally expensive.

In order to deal with this situation, an ultrasound diagnostic apparatus has also been developed in which various diagnoses can be made by preparing a plurality of replaceable piezoelectric oscillator units each having an oscillator array and detachably mounting a suitable piezoelectric oscillator unit on the ultrasound probe body.

An example of such an ultrasound diagnostic apparatus includes, as shown in JP 2009-60992 A, an ultrasound probe which has a piezoelectric oscillator unit, a housing for holding the piezoelectric oscillator unit, and a detachable element connector disposed between the piezoelectric oscillator unit and the housing.

As described above, the scan mode of the ultrasound probes differs with the site to be diagnosed. In addition, the proper frequency range may often differ with the purpose of diagnosis.

Therefore, according to an ultrasound diagnostic apparatus having replaceable piezoelectric oscillator units as described in JP 2009-60992 A, settings of the ultrasound probe used can be finely changed and optimized depending on the site to be diagnosed or the purpose of diagnosis.

An ultrasound diagnostic apparatus as described in JP 2007-275087 A which wirelessly transmits the reception signals of the ultrasound probe to the diagnostic apparatus body can have an enlarged function by a method as described in JP 2009-60992 A in which a plurality of types of replaceable piezoelectric oscillator units are detachably mounted on an ultrasound probe body depending on the site to be diagnosed or the purpose of diagnosis.

However, the ultrasound diagnostic apparatus having the replaceable piezoelectric oscillator units as described in JP 2009-60992 A cannot operate with a high flexibility by merely identifying the ultrasound probe in the diagnostic apparatus body as described in JP 2007-275087 A.

An object of the present invention is to solve the foregoing prior art problems and to provide a wireless ultrasound diagnostic system which wirelessly transmits reception signals of an ultrasound probe to a diagnostic apparatus body and is capable of flexible and smooth wireless connection between the diagnostic apparatus body and the ultrasound probe having replaceable piezoelectric oscillator units and having desired settings.

SUMMARY OF THE INVENTION

In order to achieve the above object, the present invention provides a wireless ultrasound diagnostic system including: at least one piezoelectric oscillator unit which transmits and receives ultrasonic waves, outputs reception signals in accordance with the received ultrasonic waves and has specific identification information; at least one wireless communication unit which comprises a signal processor for processing the reception signals outputted from the at least one piezoelectric oscillator unit, a wireless communication section for converting the reception signals processed in the signal processor into wireless signals and transmitting the converted reception signals and an acquisition section for acquiring the identification information of the at least one piezoelectric oscillator unit, which is detachably connected to the at least one piezoelectric oscillator unit via an electric contact, and which has specific identification information; and a diagnostic apparatus body which performs wireless communication with the at least one wireless communication unit and generates an ultrasound image in accordance with the reception signals received by the at least one piezoelectric oscillator unit, wherein the diagnostic apparatus body acquires the identification information of the at least one piezoelectric oscillator unit and the identification information of the at least one wireless communication unit to establish the wireless communication with the at least one wireless communication unit.

In the wireless ultrasound diagnostic system of the present invention, it is preferable that one of the at least one piezoelectric oscillator unit is connected to one of the at least one wireless communication unit to form a wireless ultrasound probe which an operator can hold with a hand.

Further, it is preferable that each of the at least one piezoelectric oscillator unit is a wired ultrasound probe which an operator can hold with a hand.

Further, it is preferable that wired ultrasound probes are connectable to each of the at least one wireless communication unit and a wired ultrasound probe specified by the diagnostic apparatus body is actuated.

Further, it is preferable that the diagnostic apparatus body is transportable and the wireless ultrasound diagnostic system further comprises a cart on which the at least one wireless communication unit is mounted in a fixed manner and on which the diagnostic apparatus body is detachably mounted.

Further, it is preferable that the at least one piezoelectric oscillator unit comprises two or more piezoelectric oscillator units and the at least one wireless communication unit comprises two or more wireless communication units; at least one of the two or more piezoelectric oscillator units is a wired ultrasound probe which an operator can hold with a hand; wired ultrasound probes are connectable to at least one of the two or more wireless communication units and a wired ultrasound probe specified by the diagnostic apparatus body is actuated; and the at least one of the two or more piezoelectric oscillator units is mutually connected to the at least one of the two or more wireless communication units to form a wireless ultrasound probe which an operator can hold with a hand.

Further, it is preferable that the diagnostic apparatus body is transportable and the wireless ultrasound diagnostic system further comprises a cart on which the at least one of the two or more wireless communication units to which the wired ultrasound probes are connectable is mounted in a fixed manner and on which the diagnostic apparatus body is detachably mounted.

Further, it is preferable that the diagnostic apparatus body comprises a recognition section for recognizing whether the diagnostic apparatus body is mounted on the cart.

Further, it is preferable that based on recognition results obtained from the recognition section, the diagnostic apparatus body preferentially establishes the wireless communication with the wireless ultrasound probe when the diagnostic apparatus body is not mounted on the cart and preferentially establishes the wireless communication with any of the two or more wireless communication units to which one of the wired ultrasound probes is connected when the diagnostic apparatus body is mounted on the cart.

Further, it is preferable that the diagnostic apparatus body comprises a selector for determining which communication is preferentially established, wireless communication with the wireless ultrasound probe or wireless communication with any of the two or more wireless communication units to which one of the wired ultrasound probes is connected.

Furthermore, it is preferable that the at least one wireless communication unit issues a request for stopping wireless connection to the diagnostic apparatus body when the at least one piezoelectric oscillator unit is disconnected to the at least one wireless communication unit.

According to the ultrasound diagnostic system of the invention, wireless communication is established after the diagnostic apparatus body has acquired both the identification information of the ultrasound oscillator unit and the wireless communication unit. Therefore, in the system having the replaceable piezoelectric oscillator units, connection from the piezoelectric oscillator units to the diagnostic apparatus body can be smoothly made for the ultrasound probes having desired settings, and the diagnostic apparatus body can reliably recognize the settings of the ultrasound probes.

The wireless ultrasound diagnostic system of the invention which uses the wireless ultrasound probe can also be flexibly applied to a system using replaceable or connectable probes. The wireless ultrasound diagnostic system can also be flexibly applied to a system using a wireless ultrasound probe in combination with a wired ultrasound probe.

DETAILED DESCRIPTION OF THE INVENTION

Next, the wireless ultrasound diagnostic apparatus of the invention is described in detail by referring to the preferred embodiments shown in the accompanying drawings.

Figure 1:
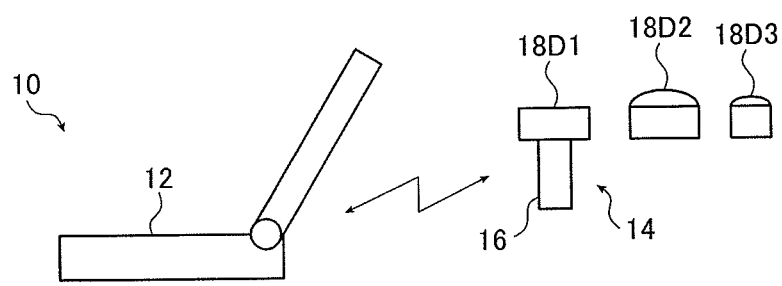
FIG. 1 is a conceptual diagram showing an embodiment of a wireless ultrasound diagnostic system of the invention.

FIG. 1 is a conceptual diagram showing an embodiment of a wireless ultrasound diagnostic system of the invention.

A wireless ultrasound diagnostic system 10 (hereinafter referred to as "diagnostic system 10") shown in FIG. 1 includes a diagnostic apparatus body 12 and a wireless ultrasound probe 14. The diagnostic apparatus body 12 is connected to the wireless ultrasound probe 14 by wireless communication and ultrasonic echo signals received by the wireless ultrasound probe 14 are transmitted by wireless communication to the diagnostic apparatus body 12.

In the illustrated preferred embodiment, the diagnostic apparatus body 12 is transportable (portable by a person).

The wireless ultrasound probe 14 (hereinafter referred to as "wireless probe 14") includes a wireless probe body 16 and piezoelectric oscillator units 18.

Each of the piezoelectric oscillator units 18 (hereinafter referred to as "oscillator units 18") is detachably mounted on the wireless probe body 16 by a connector 20 (see FIG. 2) to be described later via an electric contact. In the diagnostic system 10 shown in FIG. 1, the three oscillator units 18 including a linear scan type oscillator unit 18D1, a convex scan type oscillator unit 18D2 and a sector scan type oscillator unit 18D3 are prepared.

Figure 2:
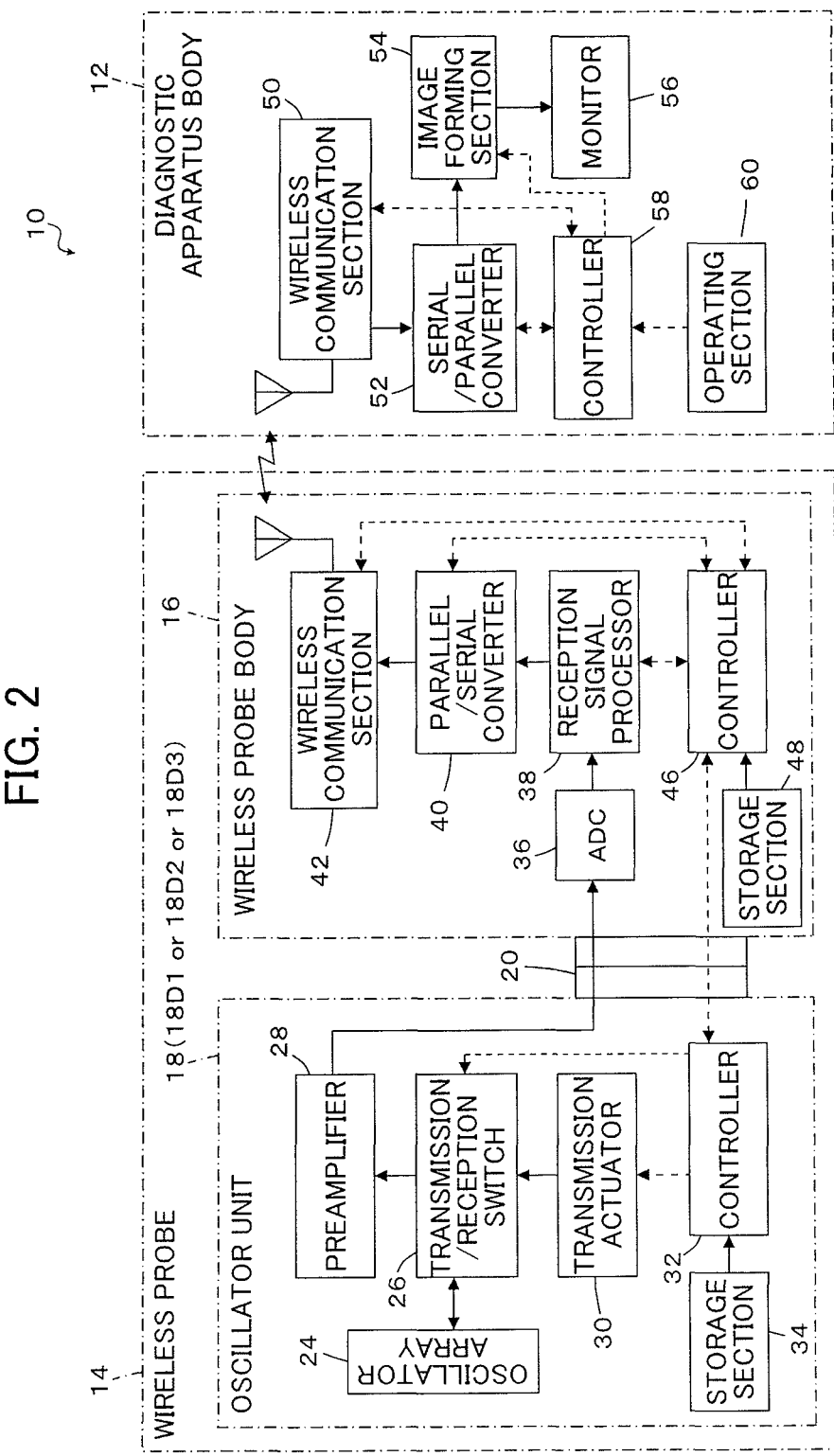
FIG. 2 is a block diagram showing the configuration of the wireless ultrasound diagnostic system shown in FIG. 1.

FIG. 2 is a block diagram showing the configuration of the diagnostic system 10.

Each oscillator unit 18 includes an oscillator array 24 which is composed of a one-dimensional or two-dimensional array of ultrasound transducers. A preamplifier 28 and a transmission actuator 30 are connected in parallel to the oscillator array 24 via a transmission/reception switch 26, and the transmission actuator 30 is connected to a controller 32. The controller 32 is further connected to a storage section 34.

On the other hand, the wireless probe body 16 includes an ADC (A/D converter (analog-digital converter circuit)) 36 which is connected to the preamplifier 28 of the oscillator unit 18 via the connector 20. The ADC 36 is connected to a reception signal processor 38, which is connected to a wireless communication section 42 via a parallel/serial converter 40.

The reception signal processor 38 and the parallel/serial converter 40 are connected to a controller 46, which is connected to the controller 32 of the oscillator unit 18 via the connector 20. The controller 46 is further connected to a storage section 48.

The ultrasound transducers making up the oscillator array 24 in the oscillator unit 18 transmit ultrasonic waves according to actuation signals supplied from the transmission actuator 30 and receive ultrasonic echoes from a subject to output reception signals.

Each of the ultrasound transducers includes an (ultrasound) oscillator having, for example, a piezoelectric body made of a piezoelectric ceramic material typified by PZT (lead zirconate titanate) or a piezoelectric polymer typified by PVDF (polyvinylidene fluoride) and an electrode provided on each end of the piezoelectric body.

When a pulsed voltage or a continuous-wave voltage is applied to the electrodes of such an oscillator, the piezoelectric body expands and contracts to cause the oscillator to generate pulsed or continuous ultrasonic waves. These ultrasonic waves are synthesized to form an ultrasonic beam. Upon reception of propagating ultrasonic waves, the oscillator expands and contracts to generate an electric signal, which is then outputted as an ultrasonic reception signal.

Under the control of the controller 32, the transmission/reception switch 26 selectively connects the oscillator array 24 to one of the preamplifier 28 and the transmission actuator 30.

The preamplifier 28 amplifies the reception signals outputted from each ultrasonic transducer of the oscillator array 24 and sends the amplified reception signals to the ADC 36 of the wireless probe body 16.

The transmission actuator 30 includes, for example, a plurality of pulsers and adjusts the delay amounts of actuation signals for the respective transducers based on a transmission delay pattern selected by the controller 32 so that the ultrasonic waves transmitted from the oscillator array 24 form a broad ultrasonic beam covering an area of a tissue of the subject and supplies the transducers in the oscillator array 24 with the adjusted actuation signals.

Based on various control signals transmitted from the controller 46 of the wireless probe body 16 which is connected to the controller 32 via the connector 20, the controller 32 controls various portions of the wireless probe 14 such as the transmission actuator 30 and the transmission/reception switch 26.

The oscillator array 24 has a specified frequency range and a specified actuation voltage.

In association therewith, the preamplifier 28 used has a frequency range which is compatible with the frequency range of the oscillator array 24 and the transmission actuator 30 used outputs an actuation voltage which is compatible with the actuation voltage of the oscillator array 24.

The controller 32 is further connected to the storage section 34.

The storage section 34 is a memory storing identification information (ID information) specific to the wireless probe 14. More specifically, the storage sections 34 of the oscillator unit 18D1, the oscillator unit 18D2 and the oscillator unit 18D3 store identification information specific to the oscillator unit 18D1, identification information specific to the oscillator unit 18D2 and identification information specific to the oscillator unit 18D3, respectively.

As described above, the reception signals amplified by the preamplifier 28 are sent to the ADC 36 of the wireless probe body 16.

The ADC 36 converts the reception signals amplified by the preamplifier 28 to digital signals.

Under the control of the controller 46, the reception signal processor 38 subjects the reception signals converted to digital signals in the ADC 36 to quadrature detection or quadrature sampling to produce complex baseband signals, samples the complex baseband signals to generate sample data containing information on the area of the tissue, and supplies the parallel/serial converter 40 with the sample data. The reception signal processor 38 may generate sample data by performing data compression for highly efficient coding on the data obtained by sampling the complex baseband signals.

The parallel/serial converter 40 converts parallel sample data generated by the reception signal processor 38 with a plurality of channels into serial sample data.

The wireless communication section 42 performs carrier modulation according to the serial sample data to generate transmission signals and supplies an antenna with the transmission signals so that the antenna transmits radio waves to achieve transmission of the sample data. The modulation methods that may be employed herein include ASK (Amplitude Shift Keying), PSK (Phase Shift Keying), QPSK (Quadrature Phase Shift Keying), and 16QAM (16 Quadrature Amplitude Modulation).

The wireless communication section 42 transmits the sample data to the diagnostic apparatus body 12 through wireless communication with the diagnostic apparatus body 12, receives various control signals from the diagnostic apparatus body 12, and outputs the received control signals to the controller 46.

Based on the control signal received from the diagnostic apparatus body 12, the controller 46 transmits a signal to the controller 32 of the oscillator unit 18 for the control of the transmission actuator 30 and also controls the wireless communication section 42 so that sample data may be transmitted at a set transmission radio field intensity.

The controller 46 is connected to the storage section 48, which is a memory storing identification information specific to the wireless probe body 16.

The connector 20 serves to detachably mount the oscillator unit 18 on the wireless probe body 16 via an electric contact and establish an electrical connection therebetween. The oscillator unit 18 is mounted on the wireless probe body 16 through the connector 20 to form the wireless probe 14. The method of mounting the oscillator unit 18 on the wireless probe body 16 using the connector 20 is not particularly limited and any known method may be used.

The connector 20 includes a reception signal line which transmits reception signals amplified by the preamplifier 28 of the oscillator unit 18 to the ADC 36 of the wireless probe body 16, and a communication line which transmits signals between the controller 32 of the oscillator unit 18 and the controller 46 of the wireless probe body 16.

The wireless probe body 16 includes a built-in battery (not shown) and power is supplied from the battery to the circuits in the oscillator unit 18 and the wireless probe body 16 of the wireless probe 14.

As described above, in the illustrated diagnostic system 10, the three oscillator units 18 including the linear scan type oscillator unit 18D1, the convex scan type oscillator unit 18D2 and the sector scan type oscillator unit 18D3 are prepared.

In the illustrated embodiment, the oscillator unit 18D1 is mounted on the wireless probe body 16 to form the wireless probe 14 of a linear scan type. The oscillator unit 18D2 is mounted on the wireless probe body 16 to form the wireless probe 14 of a convex scan type. In addition, the oscillator unit 18D3 is mounted on the wireless probe body 16 to form the wireless probe 14 of a sector scan type.

Therefore, the diagnostic system 10 which uses the single wireless probe body 16 can have the wireless probe 14 of the three types including linear scan type, convex scan type and sector scan type.

In the practice of the invention, the oscillator unit 18 is not limited to these three types and an oscillator unit 18 of a different scan type from the above types (e.g., radical scan type) may be used for the ultrasound probe instead of or in addition to at least one of the three types.

The oscillator unit 18 may be one in which ultrasound transducers compatible with mutually different frequency ranges are disposed or one in which ultrasound transducers each having a piezoelectric device for harmonic reception compatible with harmonic imaging are disposed.

The number of oscillator units 18 is also not limited to three.

In this regard, the same applies to wired probes 76 to be described later.

In addition, in the illustrated preferred embodiment, the oscillator unit 18 includes the preamplifier 28 to perform the amplification in accordance with the frequency range of the oscillator array 24 and also includes the transmission actuator 30 to output the actuation voltage. However, this is not the sole case of the invention.

That is, another configuration is also possible in which the wireless probe body 16 is provided with the preamplifier 28, the transmission actuator 30 and the like, and the oscillator unit 18 includes only the oscillator array 24 and the storage section 34. However, the oscillator unit 18 preferably includes the preamplifier 28 and the transmission actuator 30 as in the illustrated embodiment because it is not necessary to provide an over-engineered preamplifier or transmission actuator in each of the corresponding oscillator units 18 which is capable of suitable transmission and reception of ultrasonic waves in accordance with the frequency range of the oscillator array 24.

The illustrated diagnostic system 10 includes one wireless probe body 16. However, the invention is not limited to this and the diagnostic system 10 may include a plurality of wireless probe bodies 16 such as ones in which the processing in the reception signal processors 38 are mutually different.

On the other hand, the diagnostic apparatus body 12 includes a wireless communication section 50, which is connected to an image forming section 54 via a serial/parallel converter 52, and the image forming section 54 is connected to a monitor 56. The wireless communication section 50, the serial/parallel converter 52 and the image forming section 54 are connected to a controller 58. In addition, the controller 58 is connected to an operating section 60 for an operator to perform input operations.

The wireless communication section 50 transmits various control signals to the wireless probe 14 through wireless communication with the wireless probe 14. The wireless communication section 50 demodulates the signal received by the antenna to output serial sample data.

The serial/parallel converter 52 converts the serial sample data outputted from the wireless communication section 50 into parallel sample data.

The image forming section 54 performs reception focusing on the sample data to generate image signals representing an ultrasound diagnostic image. The image forming section 54 includes a phasing adder and an image processor.

The phasing adder selects one reception delay pattern from a plurality of previously stored reception delay patterns according to the reception direction set in the controller 58 and, based on the selected reception delay pattern, provides the complex baseband signals represented by the sample data with respective delays and adds them to perform the reception focusing. By this reception focusing processing, baseband signals (sound ray signals) in which the focal points of the ultrasonic echoes are made to converge are generated.

The image processor in the image forming section 54 generates, for example, a B-mode image signal, which is tomographic image information on a tissue inside the subject, according to the sound ray signal generated by the phasing adder.

The image processor includes an STC (sensitivity time control) part and a DSC (digital scan converter). The STC part corrects the sound ray signal for the attenuation due to distance according to the depth to the reflection position of the ultrasonic waves. On the other hand, the DSC converts the sound ray signal corrected by the STC part into an image signal compatible with an ordinary television signal scanning mode (performs raster conversion) and performs required image processing such as gradation processing to generate an image signal.

Based on identification information of the oscillator unit 18 and the wireless probe body 16 sent from the wireless probe 14 (wireless probe body 16), the image forming section 54 processes the reception signals in accordance with the combination of both the identification information.

The monitor 56 displays an ultrasound diagnostic image based on image signals generated by the image forming section 54 and includes, for example, a display device such as LCD.

Based on the instruction inputted by an operator from the operating section 60, the controller 58 controls the wireless communication section 50 so that various control signals are transmitted at a set transmission radio field intensity and causes the image forming section 54 to generate image signals so that the monitor 56 displays an ultrasound diagnostic image.

Upon the ultrasound diagnosis, the controller 58 acquires the identification information of the oscillator unit 18 and the wireless probe body 16 from the wireless probe 14, establishes wireless communication between the wireless probe 14 and the diagnostic apparatus body 12 when the identification information obtained is proper, and issues an instruction to the image forming section 54 so that processing suitable to the oscillator unit 18 and the wireless probe body 16 may be performed.

The wireless ultrasound diagnostic system of the invention is described below in further detail by explaining the operation of the diagnostic system 10.

An operator mounts on the wireless probe body 16 one of the oscillator units 18 selected from the diagnostic linear scan type oscillator unit 18D1, convex scan type oscillator unit 18D2 and sector scan type oscillator unit 18D3, thereby forming the wireless probe 14.

Then, the operator inputs diagnostic information including patient information and a diagnostic order from the operating section 60 of the diagnostic apparatus body 12.

In response to the input of the diagnostic information, the controller 58 of the diagnostic apparatus body 12 issues a request for wireless connection to the controller 46 of the wireless probe body 16 through wireless communication.

Upon receipt of the request for wireless connection, the controller 46 of the wireless probe body 16 issues an instruction to the controller 32 of the oscillator unit 18 so as to read out identification information stored in the storage section 34 and transmit it to the controller 46 and acquires the identification information of the oscillator unit 18 from the controller 32.

In parallel, the controller 46 of the wireless probe body 16 reads out identification information stored in the storage section 48 of the wireless probe body 16 to acquire the identification information of the wireless probe body 16.

Upon acquisition of the identification information of the oscillator unit 18 and that of the wireless probe body 16, the controller 46 transmits the combined identification information from the wireless communication section 42 to the diagnostic apparatus body 12 through wireless communication. In cases where the oscillator unit 18 is not mounted on the wireless probe body 16, the controller 46 transmits this information in combination with the identification information of the wireless probe body 16 to the diagnostic apparatus body 12.

Upon receipt of the identification information transmitted from the wireless probe body 16, the wireless communication section 50 of the diagnostic apparatus body 12 transmits the received identification information to the controller 58.

For descriptive purposes, the identification information of the wireless probe body 16, that of the linear scan type oscillator unit 18D1, that of the convex scan type oscillator unit 18D2 and that of the sector scan type oscillator unit 18D3 are represented by W1, D1, D2 and D3, respectively, and the information indicating the case where no oscillator unit 18 is mounted on the wireless probe body 16 is represented by D0.

In the case of combined identification information of W1-D1, the controller 58 establishes and performs wireless communication between the linear scan type wireless probe 14 in which the oscillator unit 18D1 is mounted on (connected to) the wireless probe body 16, and the diagnostic apparatus body 12.

In the case of combined identification information of W1-D2, the controller 58 establishes and performs wireless communication between the convex scan type wireless probe 14 in which the oscillator unit 18D2 is mounted on the wireless probe body 16, and the diagnostic apparatus body 12.

In the case of combined identification information of W1-D3, the controller 58 establishes and performs wireless communication between the sector scan type wireless probe 14 in which the oscillator unit 18D3 is mounted on the wireless probe body 16, and the diagnostic apparatus body 12.

In contrast, in the case of combined identification information of W1-D0, no oscillator unit 18 is mounted on the wireless probe body 16 and therefore the controller 58 terminates the wireless communication between the diagnostic apparatus body 12 and the wireless probe body 16.

In the case of the combined identification information of W1-D0, the termination of the wireless communication may be followed by sounding of a warning alarm or display of a message "No oscillator unit is mounted on the wireless probe body" on the monitor 56.

Upon establishment of wireless communication between the diagnostic apparatus body 12 and the wireless probe 14 (wireless probe body 16), the monitor 56 displays a message indicating that the diagnosis is possible in response to an instruction from the controller 58 so that the operator may issue an instruction for starting an ultrasound diagnosis.

In parallel with the establishment of the wireless communication, the controller 58 of the diagnostic apparatus body 12 transmits combined information including the identification information of the wireless probe body 16 and that of the oscillator unit 18 to the image forming section 54.

Upon issuance of the instruction for starting the diagnosis, the controller 58 of the diagnostic apparatus body 12 transmits an instruction for the operational control to the wireless probe 14 via the wireless communication section 50.

The wireless communication section 42 of the wireless probe body 16 receives the instruction for the operational control and sends it to the controller 46. Then, the controller 46 outputs an instruction for actuating the oscillator array 24 to the controller 32 of the oscillator unit 18 via the connector 20.

The controller 32 of the oscillator unit 18 which received this instruction causes the transmission/reception switch 26 to be operated so that the transmission actuator 30 may be connected to the oscillator array 24, and the ultrasound transducers making up the oscillator array 24 transmit ultrasonic waves according to an actuation signal supplied from the transmission actuator 30.

Thereafter, the controller 32 causes the transmission/reception switch 26 to be operated so that the preamplifier 28 is connected to the oscillator array 24, and reception signals outputted from the transducers of the oscillator array 24 that received ultrasound echoes from a subject are amplified in the preamplifier 28 before being transmitted to the wireless probe body 16 via the connector 20.

The reception signals transmitted to the wireless probe body 16 are digitized in the ADC 36 and supplied to the reception signal processor 38, where sample data is generated. The sample data is converted into a serial form in the parallel/serial converter 40 before being wirelessly transmitted from the wireless communication section 42 to the diagnostic apparatus body 12.

The sample data received by the wireless communication section 50 of the diagnostic apparatus body 12 is converted into parallel data in the serial/parallel converter 52 and transmitted to the image forming section 54.

The image forming section 54 subjects the transferred sample data to processing suitable to the diagnosis and the previously supplied, combined identification information of the wireless probe body 16 and the oscillator unit 18 to thereby generate display image signals. For example, the DSC provided in the image processor of the image forming section 54 performs image signal coordinate transformation or interpolation in accordance with the scanning mode of the oscillator unit 18 mounted in the wireless probe 14.

The display image signals generated in the image forming section 54 are sent to the monitor 56, where an ultrasound diagnostic image is displayed based on the image signals.

Figure 3:
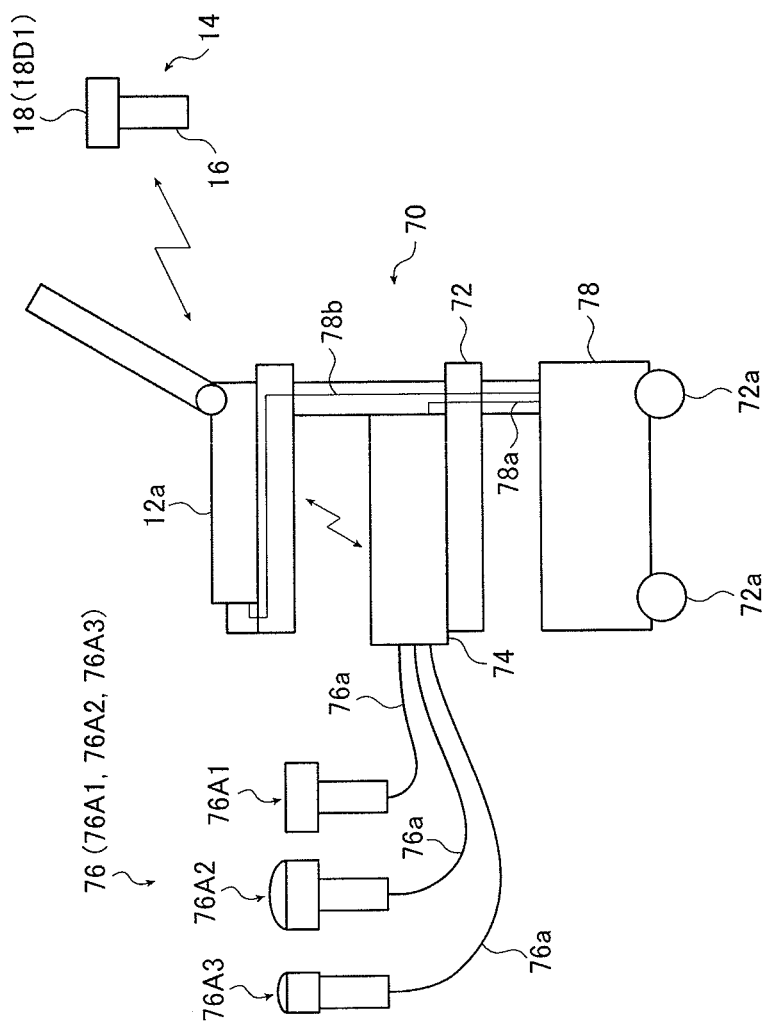
FIG. 3 is a conceptual diagram showing another embodiment of the wireless ultrasound diagnostic system of the invention.

FIG. 3 is a conceptual diagram showing another embodiment of the wireless ultrasound diagnostic system of the invention.

A wireless ultrasound diagnostic system 70 (hereinafter referred to as "diagnostic system 70") shown in FIG. 3 is a system in which wired ultrasound probes 76 can be also used in addition to the foregoing wireless probe 14. The diagnostic system 70 includes, for example, a cart 72, an intermediate processing unit 74 and the wired ultrasound probes 76 (hereinafter referred to as "wired probes 76"), in addition to a diagnostic apparatus body 12a which is basically configured in the same manner as the foregoing diagnostic apparatus body 12, and the wireless probe 14 (wireless probe body 16 and oscillator units 18D1, 18D2 and 18D3).

In the illustrated diagnostic system 70, the three wired probes 76 including a linear scan type wired probe 76A1, a convex scan type wired probe 76A2 and a sector scan type wired probe 76A3 are prepared. The wired probes 76 are not limited to these types as described above.

In the diagnostic system 70 shown in FIG. 3, the wired probes 76 are piezoelectric oscillator units in the invention and the intermediate processing unit 74 is a wireless communication unit in the invention.

Therefore, the wired probes 76 are connected to the intermediate processing unit 74.

The cart 72 is a movable carriage with wheels 72a on which the intermediate processing unit 74 is mounted in a fixed manner and the transportable diagnostic apparatus body 12a is detachably mounted.

The cart 72 has a power supply part 78, from which actuation power is supplied to the intermediate processing unit 74 via a power line 78a. When mounted on the cart 72, the diagnostic apparatus body 12a is also supplied with actuation power from the power supply part 78 via a power line 78b.

Figure 4:
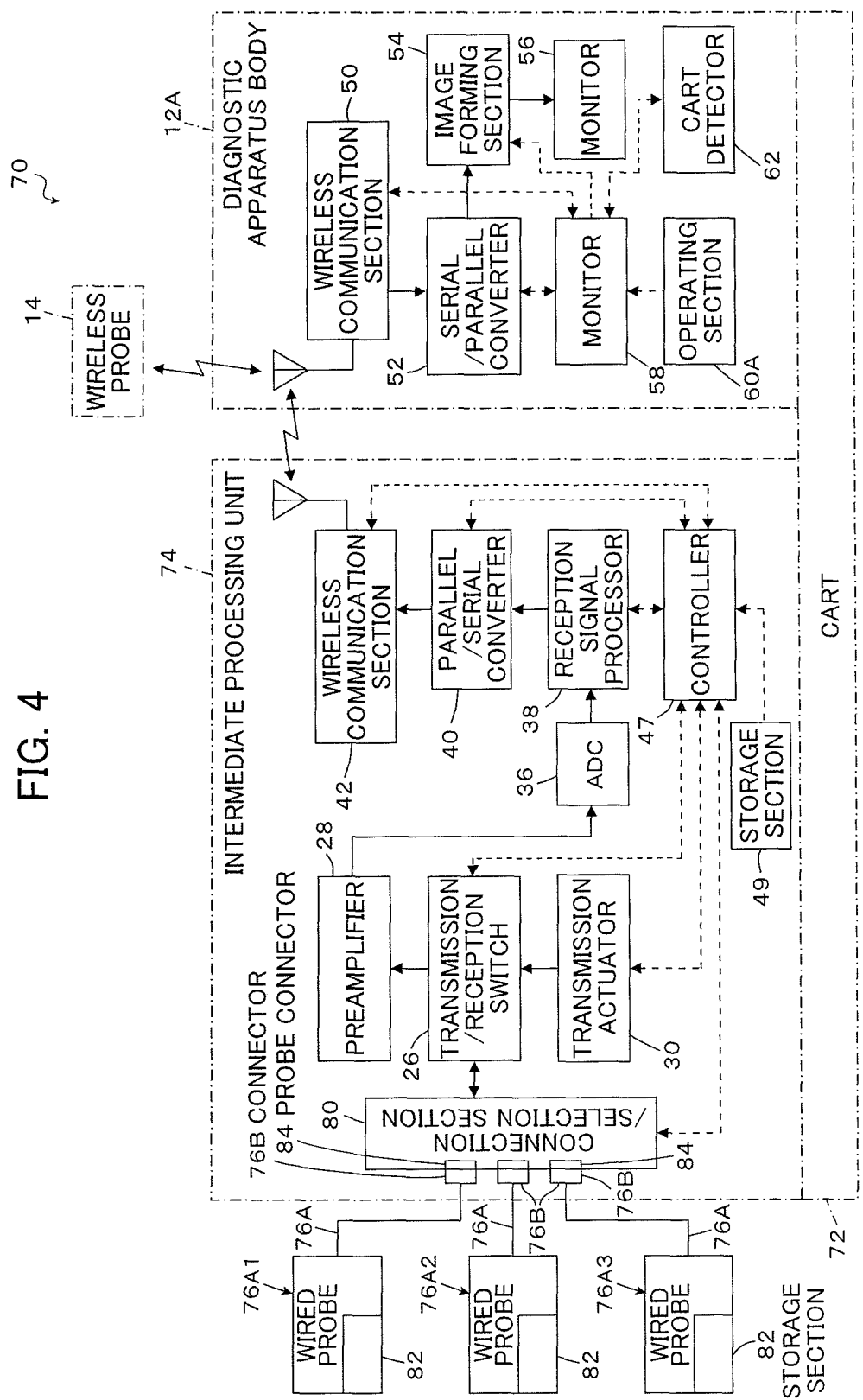
FIG. 4 is a block diagram showing the configuration of the wireless ultrasound diagnostic system shown in FIG. 3.

FIG. 4 is a block diagram conceptually showing the configuration of the diagnostic system 70.

In the diagnostic system 70, because many components in the intermediate processing unit 74 and the diagnostic apparatus body 12a are the same as those provided in the foregoing diagnostic system 10 and the mutual relationships between the components are also basically the same, like components are denoted by the same reference numerals and the following description mainly focuses on the different features.

Each of the wired probes 76 includes an oscillator array (not shown), a storage section 82, an electric signal line 76a and a connector 76b.

The oscillator array is the same type as the above-described oscillator array 24 which is composed of a one-dimensional or two-dimensional array of ultrasound transducers.

The storage section 82 is a memory storing identification information specific to the wired probe 76. The storage section 82 may be provided inside the connector 76b.

The oscillator array of the wired probe 76 is connected to the connector 76b by the electric signal line 76a. The connector 76b is mounted on (connected to) a probe connector 84 provided in a connection/selection section 80 of the intermediate processing unit 74 to be described later.

The connection between the connector 76b and the probe connector 84 causes the wired probe 76 (oscillator array) to be electrically connected to the intermediate processing unit 74 (more specifically the connection/selection section 80 to be described later).

The preamplifier 28, the transmission/reception switch 26 and the transmission actuator 30 of the oscillator unit 18 as well as the connection/selection section 80 are provided in the wireless probe body 16 of the diagnostic system 10 shown in FIG. 2 to form the intermediate processing unit 74. Therefore, a controller 47 which controls these components functions in a slightly different manner from the controller 46.

In this embodiment, a configuration in which the wired probe 76 includes the preamplifier 28, the transmission/reception switch 26 and the transmission actuator 30 can also be used.

The connection/selection section 80 includes the three probe connectors 84 for the connection with the connectors 76b of the wired probes 76.

In the practice of the invention, the number of the probe connectors 84 in the intermediate processing unit 74 for use in connecting with the wired probes 76 is not limited to three, and may be two or less, or four or more. Any known method may be used to connect the connectors 76b with the probe connectors 84.

The connection/selection section 80 is connected to the transmission/reception switch 26. The connection/selection section 80 has the probe connectors 84 on which the connectors 76b of the wired probes 76 are mounted, and selects one of the wired probes 76 for which an operating section 60a of the diagnostic apparatus body 12a established wireless communication to thereby receive or transmit signals.

In other words, in the diagnostic system 70, actuation signals are transmitted from the transmission/reception switch 26 to one of the wired probes 76 (oscillator array) selected by the connection/selection section 80, and reception signals outputted from the oscillator array are transmitted to the transmission/reception switch 26.

The transmission/reception switch 26, the transmission actuator 30, the reception signal processor 38, the parallel/serial converter 40 and the wireless communication section 42 are connected to the controller 47 which controls these components.

The controller 47 of the intermediate processing unit 74 is connected to a storage section 49. The storage section 49 is a memory storing identification information specific to the intermediate processing unit 74.

The diagnostic apparatus body 12 of the diagnostic system 10 in the previous embodiment is provided with a cart detector 62 and the operating section 60a is provided with a section for selecting any of the wired probes 76 to form the diagnostic apparatus body 12a.

The cart detector 62 detects whether the diagnostic apparatus body 12a is mounted on the cart 72.

There is no particular limitation on the method of detecting whether the diagnostic apparatus body 12a is mounted on the cart 72. For example, various known methods may be used, including a method in which a switch which is engaged when the diagnostic apparatus body 12a is mounted at a predetermined position of the cart 72 is used, a method in which magnetic force which can be detected when the diagnostic apparatus body 12a is mounted at a predetermined position of the cart 72 is used, and a method in which a connection with the power line 78b is detected.

The cart detector 62 is not an essential component of the diagnostic system 70. For example, it is not necessary to provide the cart detector 62 in the diagnostic system in which selection/input operations are to be made as to which of the wireless probe 14 and the wired probes 76 is used to make an ultrasound diagnosis.

The wireless ultrasound diagnostic system of the invention is described below in further detail by explaining the operation of the ultrasound diagnosis using the wired probes 76 in the diagnostic system 70.

The ultrasound diagnosis using the wireless probe 14 in the diagnostic system 70 may be performed in quite the same manner as described above.

An operator connects at least one of the linear scan type wired probe 76A1, the convex scan type wired probe 76A2 and the sector scan type wired probe 76A3 to the connection/selection section 80 of the intermediate processing unit 74 (probe connector(s) 84).

Then, the operator inputs diagnostic information including patient information and a diagnostic order from the operating section 60a of the diagnostic apparatus body 12a.

In response to the input of the diagnostic information, the controller 58 of the diagnostic apparatus body 12a issues a request for wireless connection to the controller 47 of the intermediate processing unit 74 through wireless communication.

Upon receipt of the request for wireless connection, the controller 47 of the intermediate processing unit 74 reads out identification information from the storage section 82 of any of the wired probes 76 connected to its corresponding probe connector 84 via the connection/selection section 80 to acquire the identification information of the wired probe 76. In parallel, the controller 47 of the intermediate processing unit 74 reads out identification information stored in the storage section 49 of the intermediate processing unit 74 to acquire the identification information of the intermediate processing unit 74.

Upon acquisition of the identification information of any of the wired probes 76 and that of the intermediate processing unit 74, the controller 47 transmits the combined identification information from the wireless communication section 42 to the diagnostic apparatus body 12a through wireless communication. In cases where no wired probe 76 is connected to the connection/selection section 80, the controller 47 transmits this information in combination with the identification information of the intermediate processing unit 74 to the diagnostic apparatus body 12a.

The identification information transmitted to the diagnosis apparatus body 12a is sent from the wireless communication section 50 to the controller 58 of the diagnostic apparatus body 12a.

For descriptive purposes, the identification information of the intermediate processing unit 74, that of the linear scan type wired probe 76A1, that of the convex scan type wired probe 76A2 and that of the sector scan type wired probe 76A3 are represented by W2, A1, A2 and A3, respectively, and the information indicating the case where no wired probe 76 is connected to the intermediate processing unit 74 is represented by A0.

For example, in cases where the linear scan type wired probe 76A1 is only connected to the intermediate processing unit 74, combined identification information of W2-A1, W2-A0 and W2-A0 is transmitted to the controller 58.

In response to the reception of the combined identification information, the controller 58 establishes and performs wireless communication between the intermediate processing unit 74 combined with the wired probe 76A1 and the diagnostic apparatus body 12a.

In cases where the linear scan type wired probe 76A1 and the convex scan type wired probe 76A2 are only connected to the intermediate processing unit 74, combined identification information of W2-A1, W2-A2 and W2-A0 is transmitted to the controller 58.

In response to the reception of the combined identification information, the controller 58 causes the monitor 56 to display for the selection of any of the wired probes 76 to be used. As a result of the selection of any of the wired probes 76 in response to this request, the controller 58 establishes wireless communication with the selected wired probe 76. For example, in cases where the wired probe 76A2 is selected, the controller 58 establishes and performs wireless communication between the intermediate processing unit 74 combined with the wired probe 76A2 and the diagnostic apparatus body 12a.

In cases where the linear scan type wired probe 76A1, the convex scan type wired probe 76A2 and the sector scan type wired probe 76A3 are connected to the intermediate processing unit 74, combined identification information of W2-A1, W2-A2 and W2-A3 is transmitted to the controller 58.

In response to the reception of the identification information, the controller 58 urges any of the wired probes 76 to be selected and establishes wireless communication with the selected wired probes 76 as in the above case. For example, in cases where the wired probe 76A3 is selected, the controller 58 establishes and performs wireless communication between the intermediate processing unit 74 combined with the wired probe 76A3 and the diagnostic apparatus body 12a.

In contrast, in cases where no wired probe 76 is connected to the intermediate processing unit 74, combined identification information of W2-A0, W2-A0 and W2-A0 is transmitted to the controller 58.

In this case, the controller 58 confirms that no wired probe 76 is connected to the intermediate processing unit 74 and terminates wired communication between the diagnostic apparatus body 12a and the intermediate processing unit 74.

In this case, the termination of the wireless communication may further be followed by sounding of a warning alarm or display of a message "No wired probe is connected" on the monitor 56 as in the above embodiment.

Upon establishment of wireless communication of the diagnostic apparatus body 12a with the wired probe 76 and the intermediate processing unit 74, the controller 58 optionally causes the monitor 56 to display a message indicating that the diagnosis is possible so that the operator may issue an instruction for starting an ultrasound diagnosis.

In parallel with the establishment of the wireless communication, the controller 58 of the diagnostic apparatus body 12a transmits combined information including the identification information of the wired probe 76 and that of the intermediate processing unit 74 to the image forming section 54.

Upon issuance of the instruction for starting the diagnosis, the controller 58 of the diagnostic apparatus body 12a transmits an instruction for the operational control to the intermediate processing unit 74 via the wireless communication section 50.

The wireless communication section 42 of the intermediate processing unit 74 receives the instruction for the operational control and transmits it to the controller 47.

Upon reception of this instruction, the controller 47 issues an instruction to the connection/selection section 80 so as to supply an actuation signal to the wired probe 76 with which wireless communication was established and to receive reception signals.

Thereafter, the controller 47 causes the transmission/reception switch 26 to be operated so that the transmission actuator 30 may be connected to the connection/selection section 80, and the ultrasound transducers making up the oscillator array of the wired probe 76 with which wireless communication was established transmit ultrasonic waves according to an actuation signal supplied from the transmission actuator 30.

Thereafter, the controller 47 causes the transmission/reception switch 26 to be operated so that the preamplifier 28 is connected to the wired probe 76 with which wireless communication was established, and the reception signals outputted from the ultrasound transducers of the oscillator array that received ultrasound echoes from a subject are amplified in the preamplifier 28 before being transmitted to the ADC 36.

The subsequent steps are the same as in the above-described diagnostic system 10, and the reception signals are digitized in the ADC 36, converted to sample data in the reception signal processor 38 and converted into a serial form in the parallel/serial converter 40 before being wirelessly transmitted from the wireless communication section 42 to the diagnostic apparatus body 12a.

The sample data received by the wireless communication section 50 of the diagnostic apparatus body 12a is converted into parallel data in the serial/parallel converter 52 and is subjected in the image forming section 54 to processing suitable to the diagnosis and the combination of the wired probe 76 with the intermediate processing unit 74, and an ultrasound diagnostic image is displayed on the monitor 56.

In other words, the diagnostic system 70 shown in FIGS. 3 and 4 is used as a wireless ultrasound diagnostic system even when the diagnostic system 70 includes no wireless probe 14 but only any of the wired probes 76.

As is clear from the above description, according to the ultrasound diagnostic system of the invention, wireless communication is established after the diagnostic apparatus body has acquired both the identification information of the ultrasound oscillator unit and the wireless communication unit. Therefore, connection from the piezoelectric oscillator units to the diagnostic apparatus body can be smoothly made for the ultrasound probes having desired settings, and the diagnostic apparatus body can reliably recognize the settings of the ultrasound probes.

Even when the oscillator unit 18 is replaceable in the wireless probe 16, the diagnostic apparatus body 12 (12a) can reliably acquire the information of the oscillator unit 18 and the wireless probe body 16. The ultrasound diagnostic system may also be advantageously applied to a system which has no wireless probe 14 and selects and uses more than one wired probe 76. In addition, the ultrasound diagnostic system may also be advantageously applied to a system which includes a wireless probe 14 in which the oscillator unit 18 is replaceable and more than one wired probe 76.

In a diagnostic system such as the diagnostic system 70 in which both of the wireless probe 14 and the wired probes 76 can be used, the operating section 60a of the diagnostic apparatus body 12a is preferably provided with a means for selecting any of the wireless probe 14 and the wired probes 76 to be used.

Also in the diagnostic system 70 in which both of the wireless probe 14 and the wired probes 76 can be used, it may be automatically selected on which of the wireless probe 14 and the wired probes 76 (and combinations with the intermediate processing unit 74) priority is to be placed for the establishment of wireless communication depending on how the diagnostic apparatus body 12a is disposed.

For example, in cases where the diagnostic apparatus body 12a is not mounted on the cart 72 based on the detection result obtained in the cart detector 62 of the diagnostic apparatus body 12a, it is highly possible that an operator carries the diagnostic apparatus body 12a and makes an ultrasound diagnosis using the wireless probe 14 beside a bed in a hospital.

Therefore, in cases where the diagnostic apparatus body 12a is not mounted on the cart 72, the controller 58 of the diagnostic apparatus body 12a first issues a request for wireless connection to the wireless probe body 16 of the wireless probe 14 and establishes a wireless connection as in the previous embodiments. In cases where no wireless communication can be established with the wireless probe body 16 (time out) or the identification information is W1-D0 (no oscillator unit is mounted), the controller 58 then issues a request for wireless connection to the intermediate processing unit 74 and establishes a wireless connection as above.

Conversely in cases where the diagnostic apparatus body 12a is mounted on the cart 72, the diagnostic apparatus body 12a moves on the cart 72 together with the intermediate processing unit 74.

In this case, the controller 58 of the diagnostic apparatus body 12a first issues a request for wireless connection to the intermediate processing unit 74 and establishes a wireless connection as above. In cases where no wireless communication can be established with the intermediate processing unit 74 (power off or time out) or the identification information is all W2-A0 (no wired probe 76 is connected to the intermediate processing unit 74), the controller 58 then issues a request for wireless connection to the wireless probe body 16 of the wireless probe 14 and establishes a wireless connection as above.

In cases where the cart 72 is provided with a probe holder, not whether the diagnostic apparatus body 12a is mounted on the cart 72 but whether the wireless probe body 16 is taken out of the wireless probe holder or whether the wired probe 76 is taken out of the wired probe holder may be detected with a sensor to determine to which a request for wireless connection is to be preferentially made, the wireless probe 14 or the intermediate processing unit 74.

There may also be a case where the diagnostic apparatus body 12a is not mounted on the cart 72 and an operator wants to use not the wireless probe 14 but the wired probe 76 (wants to communicate with the intermediate processing unit 74) and a case where the diagnostic apparatus body 12a is mounted on the cart 72 and an operator wants to use not the intermediate processing unit 74 but the wireless probe 14 (wants to communicate with the wireless probe 14).

In such cases, communication with a partner with which the communication is effective (one of the wireless probe 14 and the intermediate processing unit 74) is terminated on the diagnostic apparatus body 12a in response to a request instruction from the operator and a request for wireless connection to the desired partner is made.

In cases where the oscillator unit 18 of the wireless probe 14 is to be replaced in the diagnostic system 10 shown in FIGS. 1 and 2 or the oscillator unit 18 of the wireless probe 14 is to be replaced in the diagnostic system 70 shown in FIGS. 3 and 4 or the wired probe 76 connected to the intermediate processing unit 74 is to be changed in the diagnostic system 70 shown in FIGS. 3 and 4, the following processing steps are preferably performed.

That is, in such cases, a request for termination of wireless connection is first issued from one of the diagnostic apparatus body 12 (12a), the wireless probe body 16 and the intermediate processing unit 74 (i.e., from the portion where an instruction for a replacement request was inputted) in response to the instruction for the replacement request from the operator.

Then, the operator makes a change. Subsequently, upon issuance of a resuming instruction, a request for wireless connection is issued again from the diagnostic apparatus body 12 (12a) to the wireless probe body 16 and/or the intermediate processing unit 74. Subsequently, wireless communication is established as above in accordance with identification information acquired by the diagnostic apparatus body 12 (12a) and wireless communication according to the connection state is performed.

In a system such as the diagnostic system 70 in which the wired probes 76 and the wireless probe 14 can be used, communication between the intermediate processing unit 74 and the diagnostic apparatus body 12a may not be wireless but wired.

In such a case, the parallel/serial converter 40 and the wireless communication section 42 of the intermediate processing unit 74 are not necessary and the reception signals processed in the reception signal processor 38 may be sent to the image forming section 54 of the diagnostic apparatus body 12a or an optionally provided storage means (memory of reception signals) which is connected to the image forming section 54.

While the wireless ultrasound diagnostic system of the invention has been described above in detail, the invention is by no means limited to the above embodiments, and various improvements and modifications may be made without departing from the scope and spirit of the invention.

For example, the above embodiment includes only one intermediate processing unit 74. However, the invention is not limited to this and more than one intermediate processing unit 74 may be included.

The wireless ultrasound diagnostic system can be advantageously applied to the ultrasound diagnosis in the medical settings.

What is claimed is:

1. A wireless ultrasound diagnostic system comprising:
   at least one piezoelectric oscillator unit which transmits and receives ultrasonic waves, outputs reception signals in accordance with the received ultrasonic waves and has specific identification information;
   at least one wireless communication unit which comprises a signal processor for processing the reception signals outputted from said at least one piezoelectric oscillator unit, a wireless communication section for converting the reception signals processed in said signal processor into wireless signals and transmitting the converted reception signals and an acquisition section for acquiring the identification information of said at least one piezoelectric oscillator unit, which is detachably connected to said at least one piezoelectric oscillator unit via an electric contact with a male/female type connector, and which has specific identification information; and a diagnostic apparatus body which performs wireless communication with said at least one wireless communication unit and generates an ultrasound image in accordance with the reception signals received by said at least one piezoelectric oscillator unit, wherein said connector forms a wireless ultrasound probe which is unified by a detachable and direct connection of one of said at least one piezoelectric oscillator unit and one of said at least one wireless communication unit, wherein said diagnostic apparatus body acquires both the identification information of said at least one piezoelectric oscillator unit and the identification information of said at least one wireless communication unit of said wireless ultrasound probe to establish the wireless communication with said at least one wireless communication unit of said wireless ultrasound probe.

2. The wireless ultrasound diagnostic system according to claim 1, wherein said wireless ultrasound probe is the one which an operator can hold with a hand.

3. The wireless ultrasound diagnostic system according to claim 1, further comprising a wired ultrasound probe with one of said at least one piezoelectric oscillator unit and which an operator can hold with a hand, and a second wireless communication unit with one of said at least one wireless communication unit and which actuates said wired ultrasound probe.

4. The wireless ultrasound diagnostic system according to claim 3, wherein said second wireless communication unit is further connectable to wired ultrasound probes and actuates a wired ultrasound probe specified by said diagnostic apparatus body.

5. The wireless ultrasound diagnostic system according to claim 3, wherein said diagnostic apparatus body is transportable and wherein said wireless ultrasound diagnostic system further comprises a cart on which said second wireless communication unit is mounted in a fixed manner and on which said diagnostic apparatus body is detachably mounted.

6. The wireless ultrasound diagnostic system according to claim 1, wherein said at least one piezoelectric oscillator unit comprises two or more piezoelectric oscillator units and said at least one wireless communication unit comprises two or more wireless communication units, wherein at least one of said two or more piezoelectric oscillator units forms a wired ultrasound probe which an operator can hold with a hand, wherein at least one of said two or more wireless communication units is connectable to wired ultrasound probes and forms a second wireless communication unit which actuates a wired ultrasound probe specified by said diagnostic apparatus body, and wherein the other at least one of said two or more piezoelectric oscillator units is mutually, detachably and directly connected with a connector to the other at least one of said two or more wireless communication units to form a unified wireless ultrasound probe which an operator can hold with a hand.

7. The wireless ultrasound diagnostic system according to claim 6, wherein said diagnostic apparatus body is transportable and wherein said wireless ultrasound diagnostic system further comprises a cart on which the second wireless communication unit is mounted in a fixed manner and on which said diagnostic apparatus body is detachably mounted.

8. The wireless ultrasound diagnostic system according to claim 7, wherein said diagnostic apparatus body comprises a recognition section for recognizing whether said diagnostic apparatus body is mounted on said cart.

9. The wireless ultrasound diagnostic system according to claim 8, wherein based on recognition results obtained from said recognition section, said diagnostic apparatus body preferentially establishes the wireless communication with said wireless ultrasound probe when the diagnostic apparatus body is not mounted on said cart and preferentially establishes the wireless communication with said second wireless communication unit to which one of said wired ultrasound probes is connected when the diagnostic apparatus body is mounted on said cart.

10. The wireless ultrasound diagnostic system according to claim 6, wherein said diagnostic apparatus body comprises a selector for determining which communication is preferentially established, wireless communication with said wireless ultrasound probe or wireless communication with said second wireless communication unit to which one of said wired ultrasound probes is connected.

11. The wireless ultrasound diagnostic system according to claim 1, wherein said at least one wireless communication unit issues a request for stopping wireless connection to said diagnostic apparatus body when said at least one piezoelectric oscillator unit and said at least one wireless communication unit which form said wireless ultrasound probe are disconnected to each other.

12. The wireless ultrasound diagnostic system according to claim 1, wherein specific information associated with the piezoelectric oscillator unit and specific information associated with the at least one wireless communication unit differ from each other.

13. A wireless ultrasound diagnostic system comprising:
at least one piezoelectric oscillator unit, having a preamplifier and a transmission actuator, which transmits and receives ultrasonic waves, outputs reception signals in accordance with the received ultrasonic waves and has specific identification information;

at least one wireless communication unit which comprises a signal processor for processing the reception signals outputted from said at least one piezoelectric oscillator unit, a wireless communication section for converting the reception signals processed in said signal processor into wireless signals and transmitting the converted reception signals and an acquisition section for acquiring the identification information of said at least one piezoelectric oscillator unit, which is detachably connected to said at least one piezoelectric oscillator unit via an electric contact with a male/female type connector, and which has specific identification information; and a diagnostic apparatus body which performs wireless communication with said at least one wireless communication unit and generates an ultrasound image in accordance with the reception signals received by said at least one piezoelectric oscillator unit, wherein said connector forms a wireless ultrasound probe which is unified by a detachable and direct connection of one of said at least one piezoelectric oscillator unit and one of said at least one wireless communication unit, wherein said diagnostic apparatus body acquires both the identification information of said at least one piezoelectric oscillator unit and the identification information of said at least one wireless communication unit of said wireless ultrasound probe to establish the wireless communication with said at least one wireless communication unit of said wireless ultrasound probe.

14. The wireless ultrasound diagnostic system according to claim 13, wherein said wireless ultrasound probe is the one which an operator can hold with a hand.

15. The wireless ultrasound diagnostic system according to claim 13, further comprising a wired ultrasound probe with one of said at least one piezoelectric oscillator unit and which an operator can hold with a hand, and a second wireless communication unit with one of said at least one wireless communication unit and which actuates said wired ultrasound probe.

16. The wireless ultrasound diagnostic system according to claim 15, wherein said second wireless communication unit is further connectable to wired ultrasound probes and actuates a wired ultrasound probe specified by said diagnostic apparatus body.

17. The wireless ultrasound diagnostic system according to claim 15, wherein said diagnostic apparatus body is transportable and
wherein said wireless ultrasound diagnostic system further comprises a cart on which said second wireless communication unit is mounted in a fixed manner and on which said diagnostic apparatus body is detachably mounted.

* * * * *